United States Patent [19]

Moody et al.

[11] 4,405,608
[45] Sep. 20, 1983

[54] NOVEL PEPTIDE

[75] Inventors: Alister J. Moody, Skovbovej; Lars Thim, Skiftevej; Karin D. Jørgensen, Skovvej, all of Denmark

[73] Assignee: Novo Industri A/S, Denmark

[21] Appl. No.: 296,839

[22] Filed: Aug. 27, 1981

[51] Int. Cl.$^3$ .................... C07C 103/52; A61K 35/39; A61K 35/38; A61K 37/02
[52] U.S. Cl. .................................. 424/177; 424/110; 424/104; 260/112.5 R
[58] Field of Search ...................... 424/177, 104, 110; 260/112.5 R

[56] References Cited

U.S. PATENT DOCUMENTS

| 81,681 | 8/1868 | Tanabe | 424/110 |
|---|---|---|---|
| 2,115,418 | 4/1938 | Dragstedt | 424/110 |
| 3,493,399 | 2/1970 | Levin | 424/110 |
| 3,803,305 | 5/1972 | Thuillier | 424/110 |

Primary Examiner—Delbert R. Phillips
Assistant Examiner—F. T. Moezie
Attorney, Agent, or Firm—Fidelman, Wolffe & Waldron

[57] ABSTRACT

A novel, purified peptide having the following amino acid sequence:
Arg-Ser-Leu-Gln-Asn-Thr-Glu-Glu-Lys-Ser-Arg-Ser-Phe-Pro-Ala-Pro-Gln-Thr-Asp-Pro-Leu-Asp-Asp-Pro-Asp-Gln-Met-Thr-Glu-Asp.

The peptide may be used as medicament, e.g., in the treatment of gastroduodenal ulcers.

4 Claims, No Drawings

NOVEL PEPTIDE

The present invention relates to a purified peptide (herein designated GRPP) and salts thereof, to a process for preparing GRPP and salts thereof, to the use of GRPP and physiologically acceptable salts thereof as a medicament and to pharmaceutical compositions containing GRPP or physiologically acceptable salts thereof.

Underlying the present invention is the fact that GRPP and salts thereof show interesting pharmacological properties, for example an inhibition of the gastric acid secretion.

GRPP is a peptide having the following amino acid sequence:

Arg—Ser—Leu—Gln—Asn—Thr—Glu—Glu—Lys—Ser—
                                    5                                10

—Arg—Ser—Phe—Pro—Ala—Pro—Gln—Thr—Asp—Pro—
                    15                                        20

—Leu—Asp—Asp—Pro—Asp—Gln—Met—Thr—Glu—Asp.
                        25                                     30

The molecular weight of GRPP as calculated from the amino acid content is 3445 and the isoelectric point of GRPP is 4.0±0.2.

RECOVERY OF GRPP

GRPP may be extracted from porcine pancreas glands. Preferably, GRPP is isolated from the mother liquor from the so-called insulin salt cake obtained in the production of insulin.

The insulin salt cake may be prepared as follows:

Whole, neatly defatted porcine pancreas glands are finely comminuted under frozen conditions and then subjected to the conventional extraction process for recovery of insulin, that is extracted with a mixture of water and a water-miscible, organic solvent, such as a lower aliphatic alkanol, for example ethanol or isopropanol, in an acid medium, for example a medium having a pH in the range of from about 1.5 to 5 when measured with a pH meter in the mixture. The acid pH is obtained by the addition of an acid, for example hydrochloric acid. In the mixture, the organic solvent is present in a concentration in the range of from about 40 to 80% (v/v) when all the components are mixed. The resulting slurry is stirred at a temperature in the range of from about 5° C. to ambient, followed by removal of the pancreas gland residue, for example by centrifugation. The extract is then neutralized to a pH in the range of from about 5 to 9, and clarified, for example by centrifugation. The extract is acidified to a pH in the range of from about 3 to 4, whereafter the extract is freed of organic solvent, for example by evaporation at reduced pressure, followed by removal of lipid compounds, for example by centrifugation. Insulin admixed with other compounds is salted out from the concentrated extract so obtained, for example by the addition of sodium chloride to a concentration in the range of from about 10 to 30% (w/v), and the precipitate formed is isolated, for example by centrifugation, thus giving the insulin salt cake.

The mother liquor from the insulin salt cake may be used as starting material for the isolation of GRPP. However, the insulin salt cake, and consequently the mother liquor, may be prepared in many other ways, vide for example Ind.Eng.Chem. 32 (1940), 908–910. Different methods are used by different insulin manufacturers, however, in all cases GRPP will probably be present in the mother liquor from the insulin salt cake.

The isolation and purification of GRPP from the above mother liquor is performed by the use of chromatography, for example anion and cation exchange chromatography, and gel filtration, and said operations are performed in a manner known per se. Isolation and purification of peptides by chromatographic techniques are so well-known in the art as to require no general discussion here of principles or of the solvents, adsorbents and conditions employed for GRPP.

The first step in the isolation may be a desalting process, for example ultrafiltration or reverse osmosis. Alternatively, an extensive dilution of the mother liquor with water, for example between about 10 and 50 times, may be performed. As a further alternative, the first step may be to precepitate out the GRPP by salting with, e.g., ammonium sulphate.

The chromatography is preferably carried out in an aqueous medium, however, water-miscible solvents such as lower alkanols may be added.

In order to carry out cation exchange chromatography, it is desirable to use an eluent having a pH in the range of from about 2 to 6. As examples of cation exchangers carboxymethylcellulose, carboxymethyl-Sephadex and SP Sephadex may be mentioned.

In order to carry out anion exchange chromatography, it is desired to use an eluent having a pH in the range from about 4 to 9. As examples of anion exchangers DEAE cellulose, DEAE Sephadex and QAE Sephadex may be mentioned.

The ion exchange chromatography is carried out by the collection of the fractions containing the majority of GRPP. The anion and cation exchange chromatography are carried out in any order. If more than one cation or anion chromatography is carried out the two operations are preferably performed with eluents having different pH-values.

The gel filtration is preferably carried out in volatile buffers such as weak acetic acid, ammonium bicarbonate or ammonium formate. As examples of columns "Bio-gel P 10" and "Sephadex G 50" may be mentioned.

It may be desired, furthermore, to perform a preparative HPLC (high pressure liquid chromatography).

The final product may be recovered by lyophilization.

Instead of isolating GRPP from the above mother liquor, GRPP may be isolated directly from the aqueous, acidic extract of porcine pancreas glands containing a water-miscible, organic solvent by the use of ion exchange chromatography in analogy with the above processes.

Examples of salts of GRPP are salts with cations such as sodium, potassium, magnesium, calcium and zinc, and acid addition salts with organic or inorganic acids such as formic, methansulfonic, hydrochloric and sulphuric acid. Physiologically acceptable salts of GRPP are preferred. The salts may be prepared from GRPP and the cation or acid in question in any suitable manner. Such methods are known to the skilled art worker.

PROPERTIES OF GRPP

It has, surprisingly, been found that GRPP inhibits pentagastrin stimulated gastric acid secretion in rats and in cats in vivo.

In male Wistar rats, weighing about 200 g, with chronic gastric fistulas, gastric secretion was collected over periods of 30 minutes and titrated with 0.01 N sodium hydroxide. 10 µg pentagastrin was administered subcutaneously in 1 ml of 0.9% saline with 0.1% human serum albumin (HSA). 1.9 ml of 0.9% saline with 0.1% HSA or 5 µg GRPP or 10 µg GRPP in saline with HSA was administered intravenously over 1 hour in crossover experiments. The infusions were started when the pentagastrin was administered.

In one experiment (N=three rats) the pentagastrin administration combined with placebo caused an average increase in acid secretion over basal acid secretion (before pentagastrin administration) of 12.5 µEq acid. Pentagastrin plus 5 µg GRPP gave an increase of 6.0 µEq acid and pentagastrin plus 10 µg GRPP an increase of 0.5 µEq acid. (Eq herein designates equivalent.)

In male and female cats, weighing 2.8–4.2 kg, with chronic gastric fistulas the gastric acid secretion was stimulated with pentagastrin. Gastric secretion was collected over periods of 15 minutes and titrated with 0.01 N sodium hydroxide. The increase in acid secretion after the administration of pentagastrin was calculated as µEq acid excreted over 90 minutes after the administration, subtracting the basal acid secretion before the injection of pentagastrin. In two cats, the subcutaneous administration of 1 µg/kg pentagastrin in 1 ml of 0.9% saline with 0.1% HSA at the same time as the subcutaneous administration of 1 ml placebo (saline with HSA) caused an increase in acid secretion over basal acid secretion of $854 \pm 83$ µEq acid ($\bar{x} \pm $S.E.M., N=16 experiments). The administration of the same dose of pentagastrin at the same time as subcutaneous administration of 2 µg/kg GRPP caused an increase of $555 \pm 28$ µEq acid (N=3 experiments). For comparison it can be mentioned that pentagastrin plus 2 µg/kg glucagon and 3 µg/kg glucagon caused an increase of 632 µEq acid and 21 µEq acid, respectively, in the same cats. In two other cats, 5 µg/kg pentagastrin plus placebo gave an increase in gastric acid secretion of $1229 \pm 145$ µEq acid (N=9 experiments), whereas 5 µg/kg pentagastrin plus 16 µg/kg GRPP caused a mean increase of 616 ‖ Eq acid (N=2 experiments). For comparison it can be mentioned that 5 µg/kg pentagastrin plus 16 µg/kg glucagon gave an increase of 185 µEq acid.

Therefore, GRPP can be used to control the gastric acid secretion in mammals, for example in man. This means that GRPP may be used in the treatment of gastroduodenal ulcer diseases in man.

USE OF GRPP

The dosage rates of GRPP and salts thereof can be adjusted according to the magnitude of desired response and with other factors generally taken into consideration in establishing prescription of a particular dosage. As an example of a dosage range, from 1 to 500 µg, preferably from 10 to 50 µg, per kg body weight is suitable, although a lower or higher dosage may be administered safely. An isotonic solution dosage form of GRPP may contain from 60 µg/ml to 30 mg/ml, preferably from 0.6 mg/ml to 3 mg/ml.

GRPP and salts thereof are converted into pharmaceutical preparations and administered, preferably to humans, in analogy with known methods.

GRPP and salts thereof may be administered intraveneously, intramuscularly or subcutaneously. Furthermore, GRPP and salts thereof may be administered by the nasal or rectal route. GRPP and salts thereof may possibly be administered orally.

For the purpose of parenteral administration, GRPP or salts thereof may be dissolved in distilled water and the pH is adjusted to about 6 to 8. In order to facilitate the lyophilization process resulting in a suitable product lactose may be added to the solution. The solution is sterile filtered and filled in vials. Thereafter, the solutions are lyophilized and the vials are sealed under aseptic conditions.

For the purpose of nasal administration a solution in a nasal spraying device or nebulisator may be used. GRPP or a salt thereof is dissolved in distilled water, the pH is adjusted to about 6 to 8 by adding, for example, sodium phosphate and citric acid as buffer. Sodium chloride, sorbitol and glycerol may be used to obtain an isotonic solution with a suitable viscosity. The solution is administered by the use of a suitable nebulisator or plastic spray. The solution may be preserved by the use of known preservatives and a known surfactant may be added.

For the purpose of nasal administration by the use of dose aerosol spray GRPP may be mixed with suitable constituents and a mixture of volatile halogencarbons, for example monofluorotrichloromethane, difluorodichloromethane and tetrafluorodichloroethane in order to obtain a mixture with a vapour pressure producing a well defined single dose when the mixture is administered by the use of a dose aerosol spray.

For the purpose of rectal administration suppositories are produced by admixing GRPP or a salt thereof with an inactive constituent such as cocoa butter or with a base such as Polysorbate 85, propylene glycol monostearate and white bee's wax.

The present invention also relates to a pharmaceutical comprising purified GRPP or a salt thereof in pharmaceutically acceptable carrier(s). The carrier may be in part or entirely diluents(s) or exhipient(s). As examples of such carriers, aqueous sodium chloride can be mentioned. A convenient preparation of GRPP may be a sterile aqueous solution of GRPP or a salt thereof containing about 0.9% sodium chloride and optionally an effective amount of a preservative, such as methyl or propyl p-hydroxybenzoate or phenol.

To assure that the desired result is obtained through administration of GRPP or a salt thereof, it is advisable for preparing pharmaceutical compositions to use GRPP preparations which have been purified to a purity of at least 50%, preferably to a purity of at least 90% of GRPP or a salt thereof, on a dry substance basis.

TOXICOLOGY

Repeated subcutaneous administration of increasing doses of GRPP up to 16 µg/kg body weight to cats did not cause any adverse effects, and one may expect that the peptide is widely atoxic—in analogy with other physiologically present mammalian peptides of a similar size.

EXAMPLES

Processes for preparing GRPP and salts thereof and for preparing pharmaceutical preparations thereof are further illustrated by the following examples which, however, are not to be construed as limiting.

IMMUNO ASSAY

The distribution of GRPP during the recovery and fractionation hereinafter described was measured with the following radio immuno assay.

Antiglicentin serum R-64 (which reacts with glicentin$_{12-30}$) was used in the radio immuno assay. The immuno assay consisted of incubating 100 μl of standards of porcine glicentin, or of unknowns, with equal volumes of antiserum diluted (1:65,000) in a 1:200 dilution of non-immune rabbit serum for 72 hours. (125-I)glicentin (100 μl of a solution containing 60 pg (125-I)glicentin/ml) was then added and the incubation continued for 24 hours. The free and antibody bound (125-I)glicentin was separated by centrifugation 24 hours after the addition of 100 μl anti-rabbit IgG serum (DAKO, Copenhagen). Under these conditions R-64 did not react significantly with extracts of rat or human pancreas or with VIP, glucagon and GIP.

EXAMPLE 1

(a) Starting Material 225 kg of defatted porcine pancreas glands were finely comminuted and extracted with a mixture of water and ethanol in such a way that the content of water in the solvent was about 60% (volume/volume). The solvent was made acidic by the addition of hydrochloric acid (pH about 3.3 when measured with a pH meter in the mixture). The slurry was stirred and, thereafter, the gland residue was removed by centrifugation. The extract was neutralized to a pH of about 7 and clarified by centrifugation. The extract was acidified to a pH of about 3.5, whereafter the ethanol was removed by evaporation at reduced pressure and, thereafter, the extract was centrifugated. By the addition of about 20% sodium chloride to the extract a precipitate, i.e. the insulin salt cake, was formed, and it was removed by centrifugation, whereby the mother liquor was obtained.

(b) Precipitation with Ammonium Sulphate

To the mother liquor from step (a) (162 liters) 34 kg of solid ammonium sulphate was added. After 2 hours' stirring at 25° C., the precipitate (223 g wet weight) was collected by centrifugation.

(c) "SP-Sephadex" Chromatography

The wet precipitate was dissolved in 500 ml of 0.05 M formic acid/0.01 M sodium hydroxide buffer (pH=3.2). The solution, which had a conductivity (Λ) of 26 mS, was dialyzed 4×1 hour against 4 liters of water and diluted by adding 4 liters of 0.025 M formic acid/0.005 M sodium hydroxide buffer (pH=3.2). The solution, which had a conductivity of 4.6 mS and a pH of 2.8, was applied on a "SP-Sephadex C-25" column (supplied by Pharmacia AB, Sweden) (5×50 cm) equilibrated with 0.1 M formic acid/0.02 M sodium hydroxide buffer (pH=3.2, Λ=2.0 mS). After application of the sample, the column was eluted with a further 2 liters equilibration buffer. The remaining proteins were then eluted with a linear concentration gradient of sodium chloride (0.0–0.3 M) in equilibration buffer. Total volume of the gradient was 6 liters and the flow rate was 100 ml/hour. Fractions of 15 ml were collected and fractions Nos. 310–385 were pooled and concentrated by vacuum evaporation at 30° C. and gel-filtered on a "Bio-gel P-6" column (supplied by Bio-rad Laboratories, Richmond, California, USA) (10×50 cm) equilibrated in 0.05 M ammonium bicarbonate (pH=8.5). GRPP, which eluted as a single peak ($K_{av}=0.08$), was pooled and lyophilized. The words "Sephadex" and "Bio-gel" are Trade Marks.

(d) Preparative Isoelectric Focusing

The lyophilized powder from step (c) was dissolved in water and fractionated on a 440 ml "LKB" isoelectric focusing column (supplied by LKB, Stockholm, Sweden) with a mixture of ampholines (pH=2.5–5.0) (Acta.Chem.Scand. 20 (1966), 820–834). The sucrose gradient was prepared with a "LKB" gradient mixer (No. 8122). Dense solution: 94 g sucrose, 7.5 ml Ampholine (pH=2.5–4.0), 7.5 ml Ampholine (pH=3.5–5.0), 0.75 ml Ampholine (pH=3.5–10.0) and water ad 202 ml. Light solution: 2.5 ml Ampholine (pH=2.5–4.0), 2.5 ml Ampholine (pH=3.5–5.0), 0.25 ml Ampholine (pH=3.5–10.0), lyophilized sample dissolved in 175 ml water, water ad 202 ml. Anode solution: 48 g sucrose, 0.8 ml phosphoric acid (87% (w/w)) and 56 ml water. Cathode solution: 40 ml water and 0.8 ml ethanolamine. Isoelectric focusing was performed with a "LKB Power Supply" (No. 2103) at a constant power of 30 W for 21 hours at 12° C. Fractions of 4.3 ml were collected and fractions Nos. 54–62 were pooled. GRPP focused as a single peak with an isoelectric point of 4.0–4.1.

The pooled fractions were refocused in a 110 ml "LKB" isoelectric focusing column with a narrow pH gradient of about 3.7–4.3. A single peak of GRPP with pI=4.0 appeared.

In order to remove sucrose and ampholines GRPP was submitted to ion-exchange chromatography on "QAE-Sephadex A-25" (supplied by Pharmacia) followed by a desalting on "Bio-gel P-6" (supplied by Bio-rad Laboratories).

The pooled fractions from the second isoelectric focusing column (21 ml) was adjusted to pH=7.4 with 75 μl 2 M TRIS (tris(hydroxymethyl)aminomethane) and applied to a "QAE-Sephadex A-25" column (1×17 cm) equilibrated with 0.173 M TRIS/0.151 M hydrochloric acid buffer (pH=7.4). The column was washed with 300 ml equilibration buffer and GRPP was eluted with 1.0 M TRIS/0.86 M hydrochloric acid buffer (pH=7.4).

Fractions containing GRPP were pooled (8.3 ml) and applied to a "Bio-gel P-6" column (2.5×90 cm) equilibrated with 0.1 M ammonium bicarbonate (pH=8.5). The GRPP-peak fractions ($K_{av}=0.08$) were pooled and lyophilized.

(e) "QAE-Sephadex" Chromatography

The lyophilized material from step (d) was dissolved in 1 ml of water. 0.5 ml thereof was added to 0.25 ml of 0.173 M TRIS/0.15 M hydrochloric acid buffer (pH=7.4) and applied to a "QAE-Sephadex A-25" column (0.7×9 cm) equilibrated with the buffer added. After application of the sample, the column was washed with 35 ml of equilibrating buffer and eluted with a chloride gradient from 0.15–1.7 M in equilibrating buffer in a total volume of 220 ml. The flow rate was 1.7 ml/hour and fractions of 1.0 ml were collected. Fractions Nos. 58–62 were pooled.

The material collected was desalted on a "Bio-gel P-30" column (supplied by Bio-rad Laboratories) (1×115 cm) equilibrated with 0.05 M ammonium bicarbonate (pH=7.0) at a flow rate of 1.6 ml/hour. The GRPP-peak was pooled and lyophilized.

The yield in each step of the purification procedure and the degree of purification obtained are summarized in Table I.

TABLE I
PURIFICATION OF GRPP

| Step | Protein mg* | GRPP mg Eq | Yield Percent | Purification times |
|---|---|---|---|---|
| (NH₄)₂SO₄—precipitate | 193,000 | 167 | 100 | 1 |
| "SP-Sephadex C-25" | 5,274 | 70 | 42 | 15 |
| Isoelectric focusing 440 ml column | 210 | 49 | 29 | 270 |
| Isoelectric focusing 110 ml column | 3.6 | 18 | 11 | 5800 |
| "QAE-Sephadex A-25" | 0.8 | 6.0 | 3.6 | 8700 |

*It was assumed that 1 mg/ml had an absorbance of 1.0 in a 1 cm cuvette at 276 nm.

The peptide isolated by the above method represents a crude non-homogeneous preparation of GRPP. A final purification of GRPP was obtained in point (f).

(f) Two-dimensional Chromatography/Electrophoresis

Approximately 450 μg Eq crude GRPP from step (e) was dissolved in 20 μl 10% (v/v) pyridine/0.3% (v/v) acetic acid (pH 6.5). The sample was applied to a 20×20 cm cellulose thin-layer plate. The plate ("Avicel" 250 μm, supplied by Anachem. Ltd. Luton) was purified before the use by ascending chromatography in 5% pyridine and 1.5% formic acid, successively. The two-dimensional chromatogram was obtained using electrophoresis in the first dimension at 50 V/cm plate length for 25 minutes at 15° C. (Shandon thin-layer electrophoresis apparatus "Mk II"). The electrophoresis buffer was 10% (v/v) pyridine/0.3% (v/v) acetic acid (pH 6.5). The solvent in the ascending chromatography in the second dimension was n-butanol/acetic acid/water/pyridine (15:3:12:10 by vol.). GRPP was localized by spraying with a solution of 0.1% ninhydrin/3% 2,4,6-collidine/10% acetic acid in ethanol. The cellulose layer corresponding to GRPP ($R_f$ value in chromatography: 0.43) was scraped off and GRPP was extracted with 2×300 μl of 50% acetic acid, and lyophilized. The product obtained represented highly purified GRPP. The words "Avicel" and "Shandon" are Trade Marks.

EXAMPLE 2

The lyophilized material from step (d) in Example 1 was dissolved in 1 ml of water and 0.5 ml thereof was added to 0.25 ml of 0.058 M TRIS/0.05 M hydrochloric acid/0.18 M sodium chloride buffer (pH 7.4). The mixture was applied to a "QAE-Sephadex A-25" column (0.7×9 cm) which was equilibrated with the buffer added. The column was eluted with equilibrating buffer, whereby GRPP eluted in 5.5 column volumes.

The purity of the product was approximately equal to the purity of the product obtained from the "QAE column" described in Example 1 (e).

The product was desalted on a "Bio-gel P-30" column, vide Example 1 (e), and may be further purified, vide the process of Example 1 (f).

EXAMPLE 3

(a) Concentration 100 liters of mother liquor corresponding to 140 kg of porcine pancreas, vide step (a) of Example 1, was concentrated to 45 liters by ultrafiltration (DDS-800 membrane, supplied from De Danske Sukkerfabrikker A/S, Copenhagen, Denmark). 45 liters of water was added and the ultrafiltration was continued until a volume of 2.6 liter was reached. This volume was kept constant by the addition of water and the ultrafiltration was continued until the conductivity of the concentrate was 3.3 mS.

(b) "SP-Sephadex" Chromatography

The pH of the concentrate was adjusted to 3.15 with 15 ml of formic acid and 0.4 liters of the following eluant was added: 100 mM formic acid/20 mM sodium hydroxide buffer (pH 3.15). The sample was applied to a "SP-Sephadex C-25" column (10×80 cm) equilibrated with the eluant at a flow rate of 600 ml/hour. The column was eluted with 10 liters of the eluant and then with a linear gradient of sodium chloride (0–0.4 M) in the eluant. The total volume of the gradient was 60 liters and fractions of 870 ml were collected. GRPP was eluted with the gradient at a molarity of sodium chloride of about 0.28 M. Fractions Nos. 47–52 were pooled.

(c) First "QAE-Sephadex" Chromatography

The pooled fractions from step (b) were dialyzed 4 hours against 25 liters of water and then 18 hours against the following eluant: 57.7 mM TRIS/50 mM hydrochloric acid buffer (pH 7.4). The pH was adjusted to 7.4 with 110 ml of 2 M TRIS and 1 liter of water was added. The solution, which had a conductivity of 4.8 mS, was applied to a "QAE-Sephadex A-25" column (2.5×50 cm) equilibrated with the above eluant at a flow rate of 50 ml/hour. After washing with 250 ml of the eluant, the column was eluted with the eluant containing 0.16 M of sodium chloride and fractions of 15 ml were collected. Fractions Nos. 91–138 were pooled and lyophilized.

(d) Isoelectric Focusing

The lyophilized powder was dissolved in 100 ml of water and dialyzed 16 hours against water. The turbid solution was filtered and fractionated on a 440 ml "LKB" isoelectric focusing column with a mixture of ampholines (pH 2.5–5.0), vide Acta Chem.Scand., supra. The dense, light, anode and cathode solutions were as described in Example 1 (d). Fractions of 3.8 ml were collected and fractions Nos. 77–87 were pooled. GRPP focused as a peak with an isoelectric pH of 4.0.

(e) Second "QAE-Sephadex" Chromatography

To the pooled fractions from point (d) 5 ml of 57.7 mM TRIS/50 mM hydrochloric acid buffer (pH 7.4) was added, and the pH of the solution was adjusted to 7.4 with 1.1 ml of 2 M TRIS. The solution (37 ml) was applied to a "QAE-Sephadex A-25" column (0.7×25 cm) equilibrated with 57.7 mM TRIS/50 mM hydrochloric acid buffer (pH 7.4) at a flow rate of 1.2 ml/hour. The column was eluted with 12 ml of the above buffer and then with the buffer containing 0.16 M of sodium chloride. Fractions of 2.4 ml were collected and fractions Nos. 35–43 were pooled.

(f) Gel Filtration

The pooled fractions from step (e) were lyophilized and the powder dissolved in 3 ml of 50 mM ammonium hydrogencarbonate (pH 7.8). The solution was gel filtered on a "Bio-gel P-10" column (1.5×97 cm) equilibrated with 50 mM ammonium hydrogencarbonate. The flow rate was 5 ml/hour and fractions of 1.67 ml were collected. Fractions Nos. 43-48 were pooled and lyophilized.

The yield in each step of the purification procedure and the degree of purification obtained are summarized in Table II.

TABLE II
PURIFICATION OF GRPP

| Step | Protein mg* | GRPP mg eqv. | Yield percent | Purification times |
|---|---|---|---|---|
| Extract | 7300000 | 125 | 100 | 1 |
| Concentrate | 229000 | 119 | 96 | 30 |
| "SP-Sephadex" | 2830 | 31 | 25 | 640 |
| "QAE-Sephadex" | 80 | 16.9 | 14 | 12300 |
| Isoelectric focusing | 24 | 14.6 | 12 | 35500 |
| "QAE-Sephadex" | 2.9 | 11.5 | 9 | 232000 |
| "Bio-gel P-10" | 0.56 | 10.8 | 8 | 1130000 |

*vide Table I.

The purity of GRPP was about 95% by HPLC (high pressure liquid chromatography) on a "$\mu$Bondapak $C_{18}$ column" (supplied by Waters Association).

EXAMPLE 4

A single procine pancreas (62 g) was homogenized in 372 ml of 66% ethanol containing 0.36% phosphoric acid. After 1 hour's mixing at room temperature, the extract was centrifuged. The supernatant was collected and the tissue re-extracted with 100 ml of 60% ethanol containing 0.3% phosphoric acid. The pooled supernatants (400 ml) were clarified by passage through "Hi-Flo" (trade mark). GRPP was adsorbed from the extract by adding 1.3 g of dry "SP C-25 Sephadex" to the extract and stirring. After 1 hour a further 1.3 g of "SP C-25 Sephadex" were added. The "SP Sephadex" was removed from the extract by filtration and washed on the filter successively with 30 ml 60% ethanol/0.3% phosphoric acid and with 30 ml 60% ethanol/60 ml water and then sucked dry. The dry "SP Sephadex" was suspended in 2×15 ml of ammonium chloride solution (1 mol/l), pH 8.0, and the suspension filtered to collect the GRPP-rich filtrate. The "SP Sephadex" was washed once on the filter with 10 ml of ammonium chloride solution (1 mol/l), pH 8.5, and the filtrates combined. GRPP was precipitated by adding 19 g of ammonium sulphate to the filtrate (38 ml) and centrifuging after 1 hour's standing at room temperature. The yield of GRPP was 49 $\mu$g.

This material may be further purified, for example, by the process described in Example 1 or 3.

EXAMPLE 5

A preparation for parenteral administration containing 1 mg of GRPP per ml may be prepared as follows:

1 g of GRPP and 99 g of lactose are dissolved in 1 liter of distilled water, sodium chloride is added to isotonia and the pH-value is adjusted to 7.0. The solution is thereafter sterile filtered. The sterile solution is filled in 2 ml vials in such a way that each vial contains 1.0 ml of the sterile solution. Thereafter, the solutions are lyophilized and the vials are sealed under aseptic conditions.

The preparation in any of the vials is to be dissolved in 1.0 ml of sterile, distilled water. To humans 1 ml of said solution may be administered.

EXAMPLE 6

A preparation for parenteral administration containing 10 mg of GRPP per ml may be prepared as follows:

10 g of GRPP and 90 g of lactose are dissolved in 1 liter of distilled water and the solution is prepared analogously to the method described in Example 5.

EXAMPLE 7

Rectal suppositories are prepared by admixing 1 mg of GRPP with 4 g of cocoa butter.

EXAMPLE 8

A solution for administration by a nasal plastic spray may be prepared as follows:

0.5 g of GRPP is dissolved in about 95 ml of 0.01 M phosphate buffer (pH-value: 7.4) which is made isotonic by the addition of glycerol. The solution is preserved by the addition of 0.01% benzalkonium chloride and 0.05% EDTA whereafter 0.5% "Tween 80" is added. An isotonic phosphate buffer is added in order to give a resulting volume of 100 ml and the solution is sterile filtered. 15 ml of said solution is filed in a plastic spray giving a dose of 0.5 mg of GRPP, when activated.

We claim:

1. A purified peptide having the following amino acid sequence:

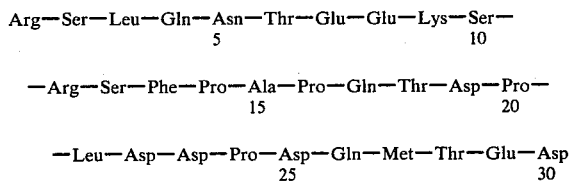

and the physiologically acceptable salts thereof.

2. A pharmaceutical composition for treatment of ulcer comprising an effective amount of the peptide having the following amino acid sequence:

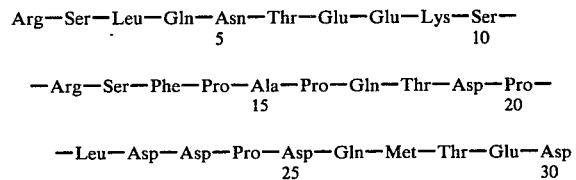

or a physiologically acceptable salt thereof in a carrier.

3. The pharmaceutical composition of claim 2 further comprising an isotonic solution containing therein from 60 $\mu$g/ml to 30 mg/ml of said peptide or salt.

4. The pharmaceutical composition of claim 2 further comprising an isotonic solution containing therein from 0.6 mg/ml to 3 mg/ml of said peptide or salt.

* * * * *

UNITED STATES PATENT AND TRADEMARK OFFICE
CERTIFICATE OF CORRECTION

PATENT NO. : 4,405,608
DATED : 9/20/83
INVENTOR(S) : ALISTER JAMES MOODY et al.

It is certified that error appears in the above-identified patent and that said Letters Patent are hereby corrected as shown below:

On the title page between lines [22] and [51] add:

[30] Foreign Application Priority Data

August 28, 1980 [DK] Denmark 3663/80

Signed and Sealed this

Twenty-eighth Day of August 1984

[SEAL]

Attest:

GERALD J. MOSSINGHOFF

Attesting Officer

Commissioner of Patents and Trademarks